United States Patent [19]

Abbott et al.

[11] Patent Number: 4,699,887

[45] Date of Patent: Oct. 13, 1987

[54] ELECTROCHEMICAL DETERMINATION OF HEMATOCRIT

[75] Inventors: Scot D. Abbott, Wilmington, Del.; Herman W. Levin, Philadelphia, Pa.; Robert K. Kobos, Wilmington, Del.; Henn Kilkson, Wilmington, Del.; Dale R. Peterson, Wilmington, Del.

[73] Assignee: E. I. Du Pont de Nemours and Company, Wilmington, Del.

[21] Appl. No.: 814,404

[22] Filed: Mar. 24, 1986

Related U.S. Application Data

[62] Division of Ser. No. 657,944, Oct. 4, 1984, Pat. No. 4,605,628.

[51] Int. Cl.$^4$ ............................................. G01N 33/86
[52] U.S. Cl. ..................................... 436/70; 436/56; 436/63; 73/61 R
[58] Field of Search ........................... 436/70, 63, 56; 73/61 R, 149, 61.4; 422/73

[56] References Cited

U.S. PATENT DOCUMENTS

| | | | |
|---|---|---|---|
| 3,648,160 | 3/1972 | Beaver | 436/70 |
| 3,964,294 | 6/1976 | Shair et al. | 436/173 |
| 3,997,838 | 12/1976 | Shamos et al. | 324/71 |

*Primary Examiner*—S. Leon Bashore
*Assistant Examiner*—Lori-Ann Cody

[57] ABSTRACT

A method for measuring hematocrit is provided. An electrochemically detectable marker is measured before and after the ratio of red cell volume to plasma volume is decreased. The measured concentrations are used in a mathematical formula to determine hematocrit value.

4 Claims, No Drawings

ELECTROCHEMICAL DETERMINATION OF HEMATOCRIT

This is a division of application Ser. No. 657,944, filed Oct. 4, 1984, now U.S. Pat. No. 4,605,628.

TECHNICAL FIELD

This invention relates to a method for the determination of the hematocrit (Hct) of a whole blood sample in which the concentration of a marker is electrochemically measured before and after the ratio of the red cell volume to plasma volume is decreased. This ratio can be decreased by lysing the red blood cells or by volumetrically diluting the blood sample with an isotonic diluent not containing the marker.

BACKGROUND ART

The determination of the hematocrit of blood is clinically important for the detection of hemorrhage and anemia. This measurement is usually made by centrifuging a blood sample and measuring the lengths of the packed red cell column and the total blood column; i.e., red cells and plasma. The hematocrit is then calculated as the ratio of the red cell column length to the length of the total blood column. The centrifugation method provides a reasonably accurate measure of the hematocrit, but is tedious and time consuming; e.g., the so-called microhematocrit method, in which a capillary tube is filled with blood by capillary action and sealed at one end, requires centrifugation at 10,000 to 12,000 g for 5 to 10 minutes.

Another method for the determination of hematocrit utilizes a flow-through cell analyzer; i.e., a flow cytometer. This instrument has been described in various patents, including U.S. Pat. Nos. 3,275,834 to Stevens and 2,565,508 to Coulter. The actual detection in these systems can be an electrical impedance measurement or an optical measurement.

The principle utilized in electrical impedance flow cytometers; e.g., Coulter Counter, involves passing a diluted blood sample through an aperture through which a current is flowing between two electrodes. The passage of a single cell through the aperture results in a voltage pulse which is proportional in magnitude to the volume of the cell. This approach requires a precise, large dilution (1:50,000) of the blood sample and is subject to inherent errors depending on the shape and electrical resistance of the cell and coincidence loss.

In optical-based flow cytometers, as described in the Stevens patent, a diluted blood sample passes through a sensing zone which is defined by a light beam. The optical measurement detects light scattering either from external reflections from the surface of the cell, from transmitted and refracted light passing through the cells, or from diffracted light which has passed tangential to the cell surfaces. This approach suffers from the same limitations as the impedance method in that the optical signals depend on the cell shape and refractive index, as well as the cell volume. Coincidence errors can also occur. Attempts to improve these methods by diminishing these errors have been reported; e.g., W. P. Hansen, Canadian Pat. No. 1144-280.

Another method for the measurement of hematocrit is based on a conductance measurement of the blood sample as described in A. Slawinski, Biochem. J. 27, 356 (1933); J. A. Kernen et al. J. Lab. Clin. Med. 57, 635 (1961); R. H. Okada et al. IRE Transactions on Medical Electronics 1960, 188; R. E. Davis, Lab. Practice 15, 1376 (1966); and H. Kiesewetter, German Pat. No. 3202-067-A. This method is based on the principle that the conductance of a whole blood sample is inversely proportional to the cell volume. This method is subject to serious errors due to temperature changes, nonlinear calibration, and abnormally high levels of plasma proteins, electrolytes, and white cells in the blood sample.

It is an object of the present invention to provide a simple and rapid electrochemical method to estimate the hematocrit of blood which requires a minimum of sample manipulation and is not subject to errors caused by differences in cell shape and abnormal levels of electrolytes and proteins in the blood sample.

DETAILED DESCRIPTION OF THE INVENTION

According to the present invention, the hematocrit of a blood sample can be estimated by electrochemically measuring the concentration of an electrochemically detectable marker before and after the ratio of the red cell volume to the plasma volume has been decreased. Electrochemical methods which can be used include potentiometric measurement with ion-selective electrodes or amperometric measurement.

The electrochemically detectable marker can be an ion or molecule, already present in the blood, whose concentrations in the plasma volume and the red cell volume are different, e.g., $Na^+$, $K^+$, and which can be either directly or indirectly measured with a high degree of selectivity by electrochemical means. Alternatively, a marker can be added to the blood sample which does not enter the red cells and can be selectively measured electrochemically; e.g., trimethylphenyl ammonium ion or tetrapentyl ammonium ion.

The ratio of the red cell volume to the plasma volume can be decreased by lysing the red blood cells using a detergent or sonication. Alternatively, the blood sample can be diluted with an isotonic diluent which does not contain the marker.

The preferred embodiment involves measurement of sodium ion concentration potentiometrically with an ion-selective electrode before and after lysing the red blood cells. This approach has several advantages. Sodium ion is present in blood plasma volume at a high concentration; i.e., 138–150 mM, while the concentration within the red cell volume is only about 10 mM. Therefore, the major effect of lysing the cells is to dilute the sodium ion concentration. Furthermore, sodium ion can be measured selectively in blood with an ion-selective electrode. The use of the lysing procedure eliminates the need to measure or quantitatively dilute the sample. With this method, the hematocrit can be estimated using the following equation:

$$Hct = 1 - \frac{[Na^+]_{L.B.}}{[Na^+]_{W.B.}} \quad (1)$$

where $[Na^+]_{L.B.}$ is the measured sodium ion concentration after lysis and $[Na^+]_{W.B.}$ is the measured sodium ion concentration before lysis. This relationship assumes that the sodium ion concentration within the red cell volume is negligible and that the percentage of water in the plasma volume and the red cell volume is 100%. The application of a constant correction factor is required in order to obtain hematocrit values which correspond to microhematocrit values. This factor corrects for the sodium ion in the red cell volume, the water content of the plasma and red cell volume, and the trapped plasma volume in the centrifugation method. The correction factor is obtained from a regression equation determined in a comparison study of the present method and the microhematocrit method, as described in examples 1 and 2. If a marker other than $Na^+$ is used, the term "$Na^+$" in equation (1) will be replaced with "Marker". Alternatively, a more exact equation can be used which takes into account the water content of the red cell volume and the plasma volume; i.e., $$Hct = \left[1 - \frac{(Na^+)_{L.B.}}{(Na^+)_{W.B.}}\right]\left[\frac{\frac{a}{b}V_p + V_{RC}}{V_p + V_{RC}}\right] \quad (1)$$

where:
- a is the percentage of water in the plasma, typically 93%;
- b is the percentage of water in the red cell volume, typically 65%;
- $V_p$ is the plasma volume; and
- $V_{RC}$ is the red cell volume.

This relationship, when solved by successive approximation, gives hematocrit values in relatively good agreement with microhematocrit values without the need for an empirical correction factor.

When a volumetric dilution of the blood sample is made, the equation for estimating the hematocrit is $$Hct = \frac{1 + \frac{V_{add}}{V_{WB}} - \frac{(Na^+)_{BD}}{(Na^+)_{AD}}}{1 - \frac{(Na^+)_{BD}}{(Na^+)_{AD}}} \quad (2)$$

where:
- $V_{add}$ is the added diluent volume;
- $V_{WB}$ is the volume of the whole blood sample;
- $(Na^+)_{BD}$ is the measured sodium ion concentration before dilution; and
- $(Na^+)_{AD}$ is the measured sodium ion concentration after dilution.

A different correction factor is required for this method since the sodium ion within the red cell volume and the water content of the red cell volume do not have an effect. The correction factor is obtained from a regression equation determined in a comparison study of this method and the microhematocrit method, as described in example 3. If a marker other than $Na^+$ is used, the term "$Na^+$" in equation (2) will be replaced with "Marker".

EXAMPLE 1

The sodium ion concentration of freshly collected whole blood samples was measured with an electrochemical electrolyte analyzer; i.e., Nova IV [Nova Biomedical, Newton, MA]. The microhematocrit values of the samples were measured using an IEC Microhematocrit Centrifuge [International Equipment Co., Needham Hts., MA]. A second portion of the blood sample was lysed by the addition of 10 μL of an aqueous saponin solution (25% wt./vol.) for each milliliter of blood. Saponin is a detergent. It is described in U.S. Pat. No. 3,883,425 issued to Dorn on May 13, 1975. The sodium ion concentration of the lysed blood samples was measured with the Nova analyzer, and the hematocrits were calculated using equation 1. Typical results are given in Table I.

TABLE I

Typical Results from Example 1

| $Hct_{(Na+)}$ (%) | $Hct_{(Na+)}$ Corrected (%) | $Hct_{(micro)}$ (%) | Rel. Error (%) |
|---|---|---|---|
| 40.5 ± 0.2 | 48.2 | 47.7 ± 0.2 | 1.10 |
| 37.5 ± 0.1 | 44.8 | 45.3 ± 0.1 | −1.14 |
| 36.0 ± 0.4 | 43.1 | 43.2 ± 0.0 | −0.32 |
| 42.8 ± 0.3 | 50.9 | 48.9 ± 0.1 | 4.02 |
| 32.9 ± 0.2 | 39.5 | 38.3 ± 0.1 | 3.13 |
| 37.2 ± 0.7 | 44.4 | 44.9 ± 0.1 | −1.02 |
| 30.8 ± 0.3 | 37.1 | 36.3 ± 0.2 | 2.17 |
| 36.4 ± 0.3 | 43.5 | 42.9 ± 0.1 | 1.44 |
| 34.3 ± 0.2 | 41.1 | 41.5 ± 0.2 | −0.94 |
| 36.1 ± 0.5 | 43.2 | 43.9 ± 0.1 | −1.64 |
| 16.3 ± 0.1 | 20.4 | 20.3 ± 0.1 | 0.69 |
| 14.1 ± 0.2 | 17.9 | 17.9 ± 0.2 | 0.08 |

The correlation of these hematocrit values with the microhematocrits for 35 blood samples was excellent (Hct ranging from 18 to 55%); i.e., r=0.991, with a regression equation of $$Hct_{(micro)} = 1.15\, Hct_{(Na+)} + 1.73.$$

After correction using this regression equation, the average error of the method of this invention relative to the microhematocrit method was 1.8% (see Table I). Blood samples with abnormally low electrolyte levels; i.e., sodium ion concentrations of 115 mM to 120 mM, gave similar results.

EXAMPLE 2

The sodium ion concentration of freshly collected blood samples was determined with the Nova Analyzer. The microhematocrits were determined with an IEC Microhematocrit Centrifuge. A second portion of the blood samples was lysed by sonication for 10–15 seconds using a sonicating probe (Heat Systems Ultrasonics Inc., Plainview, NY), and the sodium ion concentration was remeasured. The hematocrits were calculated using equation 1. Typical results are given in Table II.

TABLE II

Typical Results from Example 2

| $Hct_{(Na+)}$ (%) | $Hct_{(Na+)}$ Corrected (%) | $Hct_{(micro)}$ (%) | Rel. Error (%) |
|---|---|---|---|
| 39.8 ± 0.3 | 48.1 | 47.7 ± 0.2 | 0.93 |
| 36.5 ± 0.2 | 44.6 | 45.3 ± 0.1 | −1.59 |
| 35.1 ± 0.7 | 43.1 | 43.2 ± 0.0 | −0.23 |
| 40.0 ± 0.2 | 48.4 | 48.9 ± 0.1 | −1.02 |
| 31.3 ± 0.1 | 39.0 | 38.3 ± 0.1 | 1.83 |
| 34.5 ± 0.5 | 42.4 | 44.9 ± 0.1 | −5.52 |
| 28.5 ± 0.1 | 35.9 | 36.3 ± 0.2 | −0.99 |
| 34.1 ± 0.1 | 42.0 | 42.9 ± 0.1 | −2.13 |
| 33.8 ± 0.4 | 40.6 | 41.5 ± 0.2 | −2.21 |
| 34.6 ± 0.5 | 42.5 | 43.9 ± 0.1 | −3.13 |
| 13.7 ± 0.7 | 20.0 | 20.3 ± 0.1 | −1.69 |
| 11.3 ± 0.1 | 17.4 | 17.9 ± 0.2 | −2.99 |

The correlation coefficient of these values with the microhematocrits was 0.987 for 35 blood samples, with a regression equation of $$Hct_{(micro)} = 1.08\, Hct_{(Na+)} + 5.16.$$

EXAMPLE 3

The sodium ion concentration of freshly collected blood samples was measured with the Nova Analyzer. The microhematocrit values were determined with an IEC Microhematocrit Centrifuge. A second portion of the blood sample was diluted (2+1) with isotonic diluent containing 27 g of glucose and 11.2 g of magnesium acetate per liter of solution. This diluent has approximately the same ionic strength and osmolarity as whole blood. The sodium ion concentration of the diluted samples was measured, and the hematocrits were calculated using equation 2. Typical results are given in Table III.

TABLE III

Typical Results from Example 3

| $Hct_{(Na+)}$ (%) | $Hct_{(Na+)}$ Corrected (%) | $Hct_{(micro)}$ (%) | Rel. Error (%) |
| --- | --- | --- | --- |
| 40.7 ± 0.8 | 46.4 | 47.7 ± 0.2 | −2.69 |
| 39.0 ± 0.4 | 44.5 | 45.3 ± 0.1 | −1.78 |
| 36.0 ± 0.8 | 41.1 | 43.2 ± 0.0 | −4.85 |
| 40.2 ± 0.5 | 45.8 | 48.9 ± 0.1 | −6.24 |
| 32.9 ± 1.5 | 37.6 | 38.3 ± 0.1 | −1.83 |
| 38.7 ± 0.1 | 44.2 | 44.9 ± 0.1 | −1.66 |
| 31.3 ± 0.5 | 35.8 | 36.3 ± 0.2 | −1.40 |
| 36.3 ± 1.6 | 41.4 | 42.9 ± 0.1 | −3.50 |
| 38.2 ± 0.4 | 43.6 | 41.5 ± 0.2 | 5.06 |
| 38.3 ± 0.5 | 43.7 | 43.9 ± 0.1 | −0.46 |
| 17.8 ± 0.6 | 20.5 | 20.3 ± 0.1 | 0.99 |
| 16.0 ± 0.2 | 18.5 | 17.9 ± 0.2 | 3.35 |

The correlation coefficient of these values with the corresponding microhematocrits was 0.982 for 35 blood samples, with a regression equation of $$Hct_{(micro)} = 1.13 \, Hct_{(Na+)} + 0.424.$$

What is claimed is:
1. A method for measuring the hematocrit of blood, Hct, comprising:
   (1) measuring concentration of a preselected electrochemically detectable marker, (Marker)WB, naturally present in a preselected volume of whole blood having an initial ratio of red cell volume to plasma volume, the concentration of marker naturally present within red cells being different from its concentration in plasma;
   (2) decreasing the ratio of red cell volume to plasma volume by lysing red cells in the preselected volume of whole blood;
   (3) measuring the marker concentration after lysing, (Marker)WB; and
   (4) calculating the hematocrit using an equation comprising the term:

$$1 - \frac{(Marker)_{WB}}{(Marker)_{WB}}$$

where:
Hct is hematocrit:
(Marker)WB is measured marker concentration after Lysis;
(Marker)WB is measured marker concentration before Lysis.

2. The method of claim 1 wherein the electrochemically detectable marker is an ion.

3. The method of claim 2 wherein the ion is selected from the group consisting of sodium ion, potassium ion, trimethylphenyl ammonium ion and tetrapentyl ammonium ion.

4. The method of claim 3 wherein the ion is sodium ion.

* * * * *